United States Patent [19]

Pang et al.

[11] Patent Number: 5,374,431
[45] Date of Patent: Dec. 20, 1994

[54] SYNTHETIC BIOADHESIVE

[75] Inventors: Roy H. L. Pang; Charles M. Cohen, both of Medway; Peter C. Keck, Millbury, all of Mass.

[73] Assignee: Creative Biomolecules, Inc., Hopkinton, Mass.

[21] Appl. No.: 988,754

[22] Filed: Dec. 10, 1992

Related U.S. Application Data

[62] Division of Ser. No. 627,323, Dec. 14, 1990, Pat. No. 5,197,973.

[51] Int. Cl.$^5$ .................. C07K 15/00; C07K 13/00; C08L 89/00; A61K 37/02
[52] U.S. Cl. ........................ 424/486; 514/2; 514/12; 514/14; 106/124; 530/300; 530/324; 530/327; 530/350
[58] Field of Search ............. 106/124; 530/300, 324, 530/327, 350; 514/2, 12, 14; 424/486

[56] References Cited

U.S. PATENT DOCUMENTS

| | | | |
|---|---|---|---|
| 4,687,740 | 8/1987 | Waite | 435/68.1 |
| 4,808,702 | 2/1989 | Waite | 530/328 |

FOREIGN PATENT DOCUMENTS

| | | |
|---|---|---|
| 0242656 | 10/1987 | European Pat. Off. . |
| 0243818 | 11/1987 | European Pat. Off. . |
| 0244688 | 11/1987 | European Pat. Off. . |
| 0308238 | 3/1989 | European Pat. Off. . |
| 0339607 | 11/1989 | European Pat. Off. . |
| 8803953 | 6/1988 | WIPO . |
| 8807076 | 9/1988 | WIPO . |

OTHER PUBLICATIONS

Waite et al., Biochem. & Biophys. Res. Comm., vol. 96, No. 4, pp. 1554–1561; "The Bioadhesive of *Mytilus Byssus:* . . . ".
Wilson et al.; MacMillan Journals, Ltd. (1981); "Structure of the hamemagglutinin membrane . . . ".
Waite et al., Biochemistry 24:5010–5014 (1985); "Peptide repeat in a mussel glue protein: theme . . . ".
Marumo et al., Elsevier Sci. Pub. B. V. (Biomed. Div) (1986) "Optimization of hydroxylation of tyrosine and . . . ".
Waite, J. H. J. of Comp. Phys., Comp. Physol B (1986) 156:491–496; "Mussel glue from *Mytilus californianus*. . . ".
Shoemaker et al., Nature, vol. 326, No. 6113 pp. 563–567 (1987); "Tests of the helix dipole model for . . . ".
Jensen et al., J. Comp. Physiol. B. 158:317–324 (1988); "The bioadhesive of *Phragmatopoma californica* . . . ".
Robin et al., Arch Ophthalmol, vol. 106 (1988); "Preliminary evaluation of the use of mussel . . . ".
Regan et al., Science, vol. 241 (1988); "Characterizations of a helical protein designed from first principles:".
Swerdloff et al., Int. J. Peptide Protein Res. 33:318–327 (1989) "Solid phase synthesis of bioadhesive analogue peptides . . . ".

(List continued on next page.)

*Primary Examiner*—Robert A. Wax
*Assistant Examiner*—Rebecca Prouty
*Attorney, Agent, or Firm*—Testa, Hurwitz & Thibeault

[57] ABSTRACT

This invention pertains to a synthetic adhesive composition for use in aqueous environments. The composition comprises polypeptide chains having an α-helical structure in aqueous environments and capable of cohesive and adhesive interactions. The polypeptide chains comprise polar and apolar amino acids, the apolar and polar amino acids being arranged to define apolar and polar vertical spiraling stripes on the helix surface. The apolar stripes allow the polypeptide chains to aggregate into superhelical structures and the polar stripes allow interchain crosslinking within and between the superhelical structures.

13 Claims, 8 Drawing Sheets

OTHER PUBLICATIONS

Williams et al., Archives of Biochem. & Biophys. vol. 269, No. 2, pp. 415–422 (1989); "Mussel glue protein has an . . . ".

Trumbore et al., Biophys. Jo. vol. 55 (1989) (abstract); "Investigations of the structure of the adhesive . . . ".

Cohen et al., Proteins: Structure, Function & Genetics 7:1–15 (1990); "a-Helical coiled coils and bundles: how to . . . ".

Kaiser, Protein Eng. (1987) pp. 193–199.

Bruccoleri et al., (1986), J. Biophysical Society, 49:79–81.

Mutter, (1988), TIB 13:260–265.

K. T. O'Neil et al. Science 250:646–651 (Nov. 1990).

J. L. Krstenansky et al. FEBS Letters. 242(2) 409–413 (Jan. 1989).

Crick, F.H.C. Acta Cryst (1953); "The packing of a-Helices:simple coiled–coils".

Dickerson et al., W. A. Benjamin Co., Inc., Menlo Park, Calif; (1969) "The structure and action of proteins".

Parry et al., J. Mol. Biol. (1977); "Structure of a-Keratin:structural implication . . . ".

```
-CCATGGCTGCTGCAGCTAAGTACAAAGCAGCCGCTGCATATAAATATGCCGCAGCTGGCTAGC
...M  A  A  A  A  K  Y  K  A  A  A  A  Y  K  Y  A  A  A  G  *
   NcoI    PstI              AlwNI              PvuII    NheI
```

Fig. 6A

```
-CCATGGCAGCAGCTGCTAAGTACAAAGCAGCCGCTGCATATAAATATGCTGCTGCAGGCTAGC
...M  A  A  A  A  K  Y  K  A  A  A  A  Y  K  Y  A  A  A  G  *
   NcoI    PvuII              AlwNI              PstI    NheI
```

Fig. 6B

```
        10         20         30         40         50         60
-CCATGGCTGCTGCAGCTAAGTACAAAGCAGCCGCTGCATATAAATATGCCGCAGCTGCTAAGT
...M  A  A  A  A  K  Y  K  A  A  A  A  Y  K  Y  A  A  A  A  K
   NcoI PstI                  AlwNI                  PvuII
                              =====                  =====

70         80         90        100
ACAAAGCAGCCGCTGCATATAAATATGCTGCTGCAGGCTAGC
 Y  K  A  A  A  A  Y  K  Y  A  A  A  A  G  *
       AlwNI                  PstI NheI
       =====                  =====
```

Fig. 7

```
-CCATGGCTGCTGCAGCTAAGTACAAAGCAGCCGCTGCATATAAATATGCCGCAG
        10        20        30        40        50
...M  A  A  A  A  K  Y  K  A  A  A  A  Y  K  Y  A  A
   NcoI        PstI              AlwNI              PvuII-

CTGCTAAGTACAAAGCAGCCGCTGCATATAAATATGCTGC
        60        70        80        90
 A  A  K  Y  K  A  A  A  A  Y  K  Y  A  A       P stI*
             AlwNI                    P|stI*
-PvuII                                           ───── INSERTION SITE

┌─────────────────────────────────────────────────────────────┐
│ TGCAGCTAAGTACAAAGCAGCCGCTGCATATAAATATGCCGCAG                │
│         100       110       120       130                   │
│  A  A  K  Y  K  A  A  A  A  Y  K  Y  A  A                  │
│ PstI              AlwNI              PvuII-                 │
│                                                             │
│ CTGCTAAGTACAAAGCAGCCGCTGCATATAAATATGCTGC TGCAGGCTAGC        │
│         140       150       160       170       180         │
│  A  A  K  Y  K  A  A  A  A  Y  K  Y  A  A  A  G  *         │
│ -PvuII             AlwNI                    P|stI* NheI     │
└─────────────────────────────────────────────────────────────┘
  PstI                                              ───── INSERTION SITE
  FRAGMENT
  INSERT
```

Fig. 8

SYNTHETIC BIOADHESIVE

This is a divisional of copending application Ser. No. 07/627,323 filed on Dec. 14, 1990, now U.S. Pat. No. 5,197,973.

BACKGROUND OF THE INVENTION

This invention relates to synthetic compositions for use as adhesives in aqueous environments. More particularly, the invention relates to biocompatible adhesive compositions.

Adhesives functional in aqueous environments have long been desired in the art. The vast majority of adhesives known to the art bind dry surfaces more strongly than the same surfaces when wet. In addition to competing with the adhesive for surface area on which to bind, water may hydrolyze or plasticize many adhesives. Of particular interest are biocompatible adhesives that function in aqueous environments, so-called "bioadhesives". It is contemplated that bioadhesives will have much utility in biomedical applications, particularly in the areas of tissue repair, drug delivery, surgery, and in vitro cell cultivation, as well as in other areas involving aqueous environments such as chromatography and marine applications.

The bioadhesives of the art are generally derived from the naturally occurring adhesive material found in marine animals, such as mussels, barnacles, and oysters. Most of the work has concentrated on the polyphenolic protein of the marine mussel *Mytilus edulis*. This bioadhesive protein is thought to be dispersed as a foam from the foot of the mussel (Waite, J. H., et al., (1985), *Biochem* 24:5010–5014), and subsequently cured to form a cohesive, adhesive material strong enough to attach the mussel to wet surfaces. The protein is characterized by a decapeptide unit repeated 75–85 times in the native molecule and having the following amino acid sequence (Sequence Listing ID No. 1):

-Ala-Lys-Pro-Ser-Tyr-Xaa$_1$-Xaa$_1$-Thr-Xaa$_2$-Lys where Xaa$_1$ is hydroxyproline and Xaa$_2$ is 3,4-dihydroxylphenylalanine (dopa). These residues are probably incorporated into the polypeptide chain as proline and tyrosine, respectively, and modified post-translationally by enzymatic hydroxylation, with the conversion of tyrosine to dopa occurring by the action of a catechol oxidase (a 'tyrosinase' enzyme) present in the byssus of the mussel (Waite, J. H., (1986) *Comp Physiol B* 156:491).

The protein apparently has a predominantly open conformation having little or no secondary structure, as determined by recent physical studies on the solution characteristics of the protein, (Trumbore, M. W. et al., *Biophys J* 55:532a (1989) and Williams, T. et al., (1989) *Ach. Biochem. Biophys.*, 269:415–422), and by application of the Chou and Fasman algorithms to the amino acid sequence, which predict an absence of α-helices or β-sheets (Williams, supra). The high concentrations of imino groups (proline, hydroxyproline), may prevent formation of substantial secondary structure within the protein.

European patent application Serial Nos. EPO 243,818 (published Nov. 4, 1987) and EPO 244,688 (published Nov. 11, 1987) describe bioadhesives comprising naturally-occurring polyphenolic protein isolated from *M. edulis*. U.S. Pat. Nos. 4,808,702 (Waite, J. H., issued Feb. 28, 1989) and 4,687,740 (Waite, J. H., issued Aug. 8, 1987) describe the isolation of decapeptides from these proteins, and methods of combining the peptides to form useful bioadhesive materials. AU 8,824,972 (published Mar. 23, 1989) describes water-impermeable adhesives comprising these repeating polyphenolic decapeptide units (10–400) and a bifunctional crosslinking agent.

EPO 242,656 (published Oct. 28, 1987); Marumo et al. (1986) *Biochem, Biophys, Acta* 872:98–103; and Swerdloff, M. D. et al, (1989) *Int. J. Peptide Protein Res.* 33:313 disclose methods for de novo synthesis of the *M. edulis* decapeptide.

PCT international patent application WO 88/03953 (published Jun. 2, 1988) describes the isolation of the genetic sequence encoding the bioadhesive precursor protein of *Mytilus edulis*.

It is an object of this invention to design a bioadhesive that simplifies the amino acid sequence required for cohesion and adhesion, and which does not rely on the repeating decapeptide unit. Another object of the invention is to provide an adhesive composition whose adhesive strength can be modulated and which may therefore be useful in a broad range of biomedical applications. It is also an object of this invention to design a polypeptide chain capable of forming a specific architecture which is cohesive and around which crosslinking can be designed. These and other objects and features of the invention will be apparent from the description, figures and claims which follow.

SUMMARY OF THE INVENTION

This invention pertains to a synthetic composition for use as an adhesive in aqueous environments. The composition comprises a plurality polypeptide chains having an α-helical structure in aqueous environments and which are capable of cohesive and adhesive interactions. As used herein, the term "cohesive" is understood to mean that two or more helical polypeptide chains of this invention are capable of aggregating into a superhelical structure such as a coiled-coil.

The amino acid sequence of each polypeptide chain comprises apolar and polar residues, the apolar and polar residues being arranged to define apolar and polar longitudinal (vertical) spiraling stripes on the helix surface. At least two apolar stripes together define a hydrophobic surface on the helix sufficient to interact with the corresponding hydrophobic surface on at least one other polypeptide chain to aggregate the chains in a superhelical structure. This superhelical "bundling" or "coiled-coil" formation is similar to the interaction between molecules of keratin, myosin or tropomyosin. The apolar amino acid residues which define the hydrophobic surface on the helix may be any apolar residues which are known to be good helix formers and which will not interfere sterically with helix or bundle formation. Useful apolar amino acids include alanine, valine, leucine and isoleucine, of which alanine residues are currently preferred.

The polar stripes on the helical polypeptide chains of this invention are interposed between apolar stripes and comprise amino acids adapted to form interchain crosslinks within and between the superhelical structures. The crosslinked composition thus forms an insoluble, cohesive matrix. Moreover, these crosslinkable residues also can form interactions with the surface to be bound by the adhesive composition of this invention in an aqueous environment. The polar stripes preferably are defined by a repeating, alternating arrangement of two different crosslinkable polar residues. In a most preferred embodiment of this invention, the polypeptide chains comprise at least three polar stripes distributed circumferentially about the helix surface.

Tyrosine and lysine are the currently preferred crosslinkable polar amino acids adapted to form interchain crosslinks. Tyrosine residues can be modified to form dopa and O-quinones which can crosslink with amino groups, such as those on the lysine residues. (Alternatively, interchain crosslinks between these or other appropriate residues may be formed using a crosslinking agent.) In addition, dopa residues are capable of chelating surface-bound metal cations, thereby displacing water from aqueous surfaces and allowing the matrix to form multiple noncovalent interactions with the surface. The sum of these noncovalent interactions is sufficient to adhere the matrix to a surface in an aqueous environment. Thus the synthetic composition of this invention provides an adhesive, cohesive matrix.

A preferred amino acid sequence of the cohesive polypeptide chains of this invention comprises one or more copies of (Sequence Listing ID No. 2):

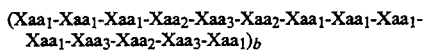
$(Xaa_1\text{-}Xaa_1\text{-}Xaa_1\text{-}Xaa_2\text{-}Xaa_3\text{-}Xaa_2\text{-}Xaa_1\text{-}Xaa_1\text{-}Xaa_1\text{-}$
$Xaa_1\text{-}Xaa_3\text{-}Xaa_2\text{-}Xaa_3\text{-}Xaa_1)_b$ where $Xaa_1$ is any helix-forming apolar amino acid; $Xaa_2$ and $Xaa_3$ are crosslinkable, surface-adherable amino acids; and b is number from 1 to 100. In general, the larger the number b, the more cohesive the matrix will be. Useful helix-forming apolar amino acids ($Xaa_1$) include, for example, alanine, valine, leucine, and isoleucine. Useful crosslinkable, surface adherable amino acids ($Xaa_2$, $Xaa_3$) include tyrosine and lysine.

In a most preferred embodiment of this invention, the amino acid sequence comprises one or more copies of (Sequence Listing ID No. 3):

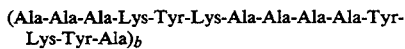
(Ala-Ala-Ala-Lys-Tyr-Lys-Ala-Ala-Ala-Ala-Tyr-Lys-Tyr-Ala)$_b$ where b is a number from 1 to 100.

As indicated above, the polypeptide chains of this invention may be crosslinked by means of a bifunctional (or multifunctional) crosslinking agent, such as a dialdehyde. A currently preferred crosslinking agent is glutaraldehyde. Alternatively, the polypeptide chains containing tyrosine and lysine may be enzymatically crosslinked by treatment with a tyrosinase enzyme.

The bioadhesives of this invention are particularly useful for bonding biologically active compounds such as cellular surfaces, and proteins. The cohesive, adhesive matrix of this invention is also useful as a delivery system for therapeutic compounds; e.g., for maintaining a therapeutic compound at a site of application in vivo. The general method comprises the steps of combining the therapeutic compound with the composition of this invention and a crosslinking agent such that the therapeutic agent becomes dispersed within the cohesive, adhesive matrix, and then applying the combination to the site of application. Similarly, the adhesive matrix of this invention may be used to maintain replacement cells at a site of application for use as a method of tissue repair such as, for example, periodontal ligament fibroblast replacement cells on the periodontal ligament surface. One can further combine a growth factor with the matrix combination to stimulate cell growth. Alternatively, the matrix may contain just a growth factor in order to stimulate cell growth at a tissue surface. Useful growth factors include EGF, PDGF, TGF-β, TGF-α, FGF and IGF.

The adhesive compounds of this invention also are useful as part of a method of sealing surgical incisions. The method includes inducing crosslinking between the molecules of this invention so that an insoluble cohesive, adhesive matrix is formed, applying this matrix to one or more surfaces at the surgical incision, and contacting the surfaces.

The adhesive and cohesive strength of the composition of this invention may be modulated by varying the length of the polypeptide chains and by varying the degree of interchain crosslinking. Altering the cohesive and adhesive strength of the composition may alter the resorption rate of the matrix in vivo, as well as the release rate of therapeutic compounds from the matrix at their site of application in vivo.

It is also contemplated that the composition of this invention will provide cohesive, adhesive matrices useful in nonbiological applications, such as in marine applications.

The polypeptide chains of this invention may be synthesized by chemical means on a peptide synthesizer, or by recombinant DNA technology and expressed in an appropriate eukaryotic or prokaryotic host system. A currently preferred host is *Escherichia coli*.

BRIEF DESCRIPTION OF THE DRAWINGS

FIGS. 6–8 illustrate gene designs useful for the recombinant production of the polypeptide chains of this invention.

DETAILED DESCRIPTION

The principles of protein folding are sufficiently well understood now that those skilled in the art can predict, with confidence, peptide sequences that are capable of forming α-helices in solution. In fact, this predictive ability has allowed the art to pursue the de novo design of complex proteins. (See, for example, Cohen et al., (1990) *Proteins* 7:1–15, or DeGrado, W. F., et al., (1988), *Science* 241:976–978.) Among the most commonly used rules or algorithms for predicting secondary structure of polypeptide chains in solution are the Chou-Fasman and Garnier-Robson catalogs of the α-helical propensities of amino acids (Chou, P. Y., et al., *Adv. Enzym.*, 1978, 47:45; Garnier, J. et al., (1978), *J. Mol. Biol* 120:87). A description of the 'rules' or conformation parameters governing helix formation are described in depth in numerous texts known to those of ordinary skill in the art (see, for example, chapters 5 and 6 of *Principles of Protein Structure*, G. E. Schulz, et al. Springer-Verlag, N.Y. 1979).

An adhesive composition for use in aqueous environments, and comprising polypeptide chains capable of forming cohesive α-helices, has now been designed. The helical polypeptide chains of this invention are capable of interacting to form superhelical structures (e.g., coiled-coils). Moreover, the polypeptide chains of this invention, contain appropriately arranged polar amino acids which are adapted to form interchain crosslinks within and between the superhelical structures (to form an insoluble crosslinked matrix), and which are also capable of interacting with the surfaces to be bonded in an aqueous environment.

Figure 1C:
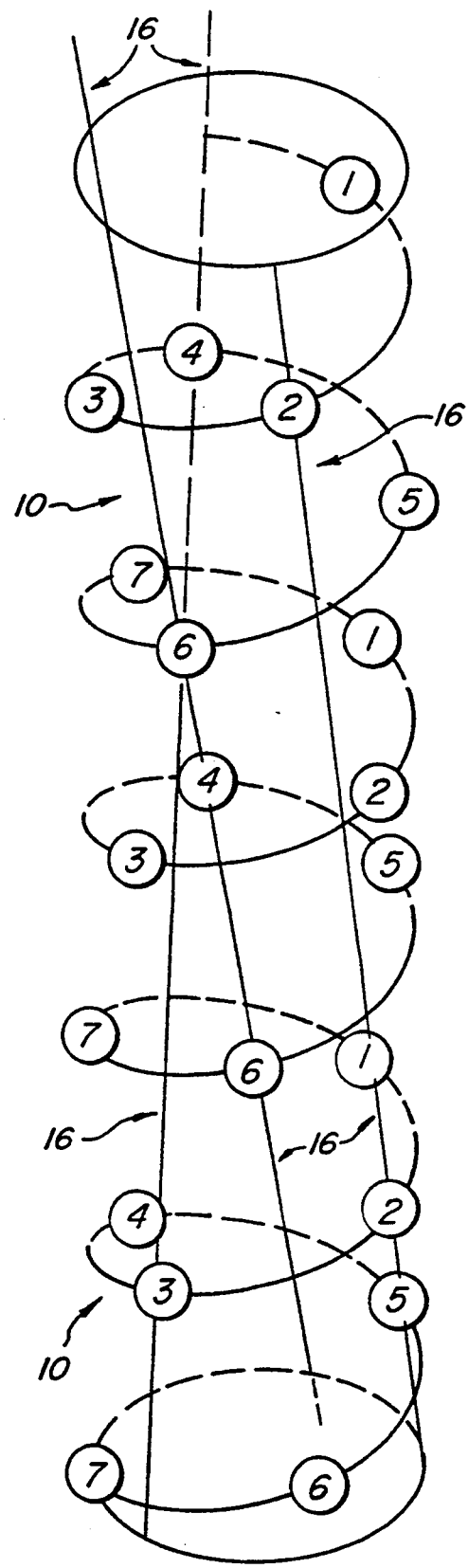
FIG. 1 (A–C) shows various schematic representations of α-helical polypeptide chains and coiled-coils.
Figure 1A:
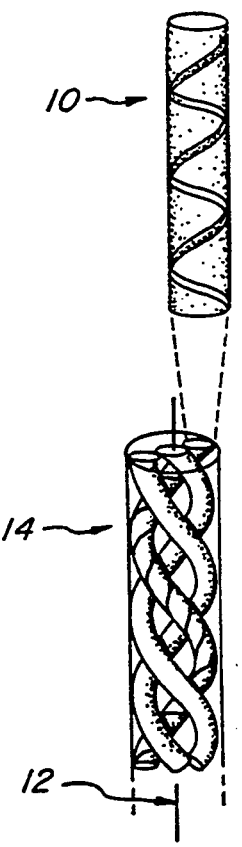
Figure 1B:
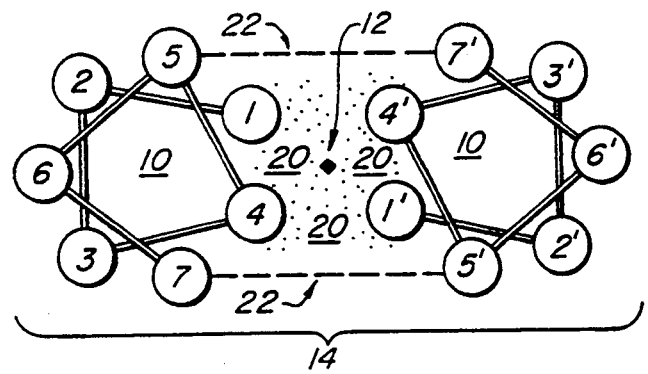

The design for the adhesive, cohesive α-helices of this invention is based in part on the known structural conformation of helix coiled-coils, such as those found in keratin, myosin, or tropomyosin. A detailed description of two-and three-stranded coiled coils can be found in Cohen et al. (1990) *Proteins* 7:1–15; Crick, F. H., (1953), *Acta Crystallogr.*, 6:689–697; Schultz, G. E. *Principles of Protein Structure*, Springer-Verlag, N.Y. 1979, and Dickerson, R. E. and Geis I., *The Structure and Action of Proteins*, W. A. Benjamin Co., Inc., Menlo Park, 1969. Briefly, and as illustrated in FIGS. 1A and 1B, three-and two-strand helix coiled-coils comprise right handed α-helices 10 that interact as strands of a rope around a central "superhelix" axis 12. Each of the helices is distorted slightly (approximately 10°) from the central axis, and the overall superhelix 14 has a left-handed twist. The geometry of each helix strand in a coil conformation is a repeating heptad, represented in FIG. 1B by the numbers 1–7 and 1′–7′. (The schematic representation of FIG. 1B looks down the superhelix axis of a two-strand coil). As a result, every seventh residue in the amino acid sequence of a given helix in a coil conformation is at a structurally equivalent position, as shown in FIG. 1C., forming a vertical (longitudinal) spiraling "stripe" 16 on the helix surface.

For α-helices to interact to form a superhelical structure, at least a portion of each helix surface must be compatible for interaction. This is most readily achieved by hydrophobic interactions between the helices. As used herein, the term "hydrophobic surface" is understood to describe a region of the helix surface sufficient to allow hydrophobic interaction between helices. The hydrophobic surface on these helices is defined by two adjacent longitudinal stripes comprising apolar amino acids, (e.g., stripes defined by residues spaced four amino acids apart in the heptad repeating sequence: 1, 4 and 1′, 4′ in FIG. 1B, the interacting hydrophobic surfaces being represented by the stippled area 20). Useful apolar amino acids can be any of the apolar amino acids, such as alanine, valine, leucine and isoleucine, that are good helix formers, and do not interfere sterically with the cohesive helix structure.

The coiled-coil structures of the art also may be stabilized by non-covalent interactions such as salt bridges between appropriate residues within corresponding stripes that flank the interacting hydrophobic surfaces (e.g., stripes defined by residues 5, 7′ and 7, 5′ in FIG. 1B, the interaction being represented by the dashed lines 22).

The polypeptide chains of this invention are designed to form an insoluble cohesive, crosslinked matrix that is stable in aqueous environments, and which can be used as an adhesive composition in this environment. The design exploits the structure of cohesive α-helices to create a specific architecture about which an adhesive, crosslinked matrix can be created. The α-helical polypeptide chains are designed to allow interchain crosslinking within and between the coiled-coils. Accordingly, the stripes defined by residues 5, 6 and 7 comprise polar crosslinkable amino acids. Interchain stabilization within a coil can occur by crosslinking between corresponding stripes (e.g., 5, 7′ and 7, 5′). Interchain crosslinking between coiled-coils can be carried out by residues in corresponding stripes defined by residue 6, so that an insoluble, crosslinked cohesive matrix of cohered superhelical structures is formed (see, for example, FIG. 2A, where solid lines 18 indicate crosslinks between superhelical structures).

The polypeptide chains of this invention also must be capable of adhering to the surface(s) to be bonded by the adhesive in an aqueous environment. In a preferred embodiment of this invention the polar crosslinkable residues are themselves the residues responsible for adhesion to these surfaces. These residues are said to be "surface adherable" or "surface adherent." In a most preferred embodiment, the polar stripes are defined by a repeating, alternating arrangement of two crosslinkable residues which also are capable of interacting with the surface to be bonded in an aqueous environment. By alternating the arrangement of the crosslinkable residues within polar stripes., the maximum number of interactions between corresponding stripes on different chains can be achieved. Location of appropriate crosslinking partners between two corresponding stripes requires only a minor shift up or down by one of the chains.

The preferred embodiment of the polypeptide chain design of this invention may be described by the generic fourteen amino acid (14-mer) sequence shown below, which is repeated one or more times in a polypeptide chain of this invention (Sequence Listing ID No. 2):

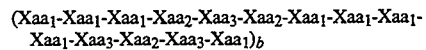

$(Xaa_1\text{-}Xaa_1\text{-}Xaa_1\text{-}Xaa_2\text{-}Xaa_3\text{-}Xaa_2\text{-}Xaa_1\text{-}Xaa_1\text{-}Xaa_1\text{-}$
$Xaa_1\text{-}Xaa_3\text{-}Xaa_2\text{-}Xaa_3\text{-}Xaa_1)_b$ where $Xaa_1$ is any helix-forming apolar amino acid; $Xaa_2$ and $Xaa_3$ are crosslinkable, surface adherable amino acids; and b is number from 1 to 100.

A currently most preferred embodiment comprises one or more copies of the following amino acid sequence (Sequence Listing ID No. 3):

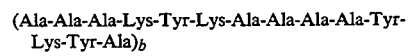

$(Ala\text{-}Ala\text{-}Ala\text{-}Lys\text{-}Tyr\text{-}Lys\text{-}Ala\text{-}Ala\text{-}Ala\text{-}Ala\text{-}Tyr\text{-}$
$Lys\text{-}Tyr\text{-}Ala)_b$ where b is a number from 1 to 100 and Ala, Lys and Tyr are alanine, lysine and tyrosine residues, respectively. Lysine and tyrosine are both polar residues which can form non-covalent interactions with the surface to be bonded, and tyrosine can be modified to form dopa, which can displace water from aqueous surfaces by chelating metal cations.

Figure 2B:
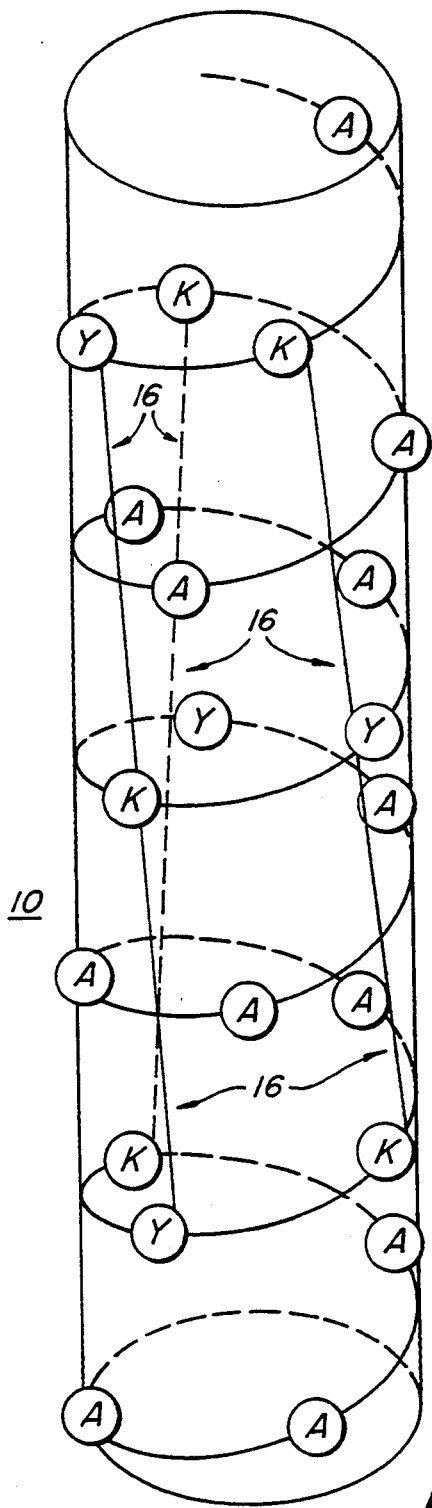
FIG. 2 (A–B) shows various schematic representations of the cohesive/adhesive polypeptide chains of this invention.
Figure 2A:
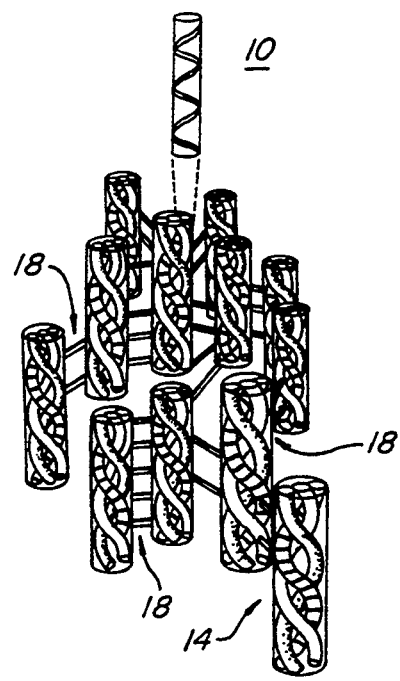

FIG. 2B is a helical representation of this preferred amino acid sequence, where b=1.5. Lines are drawn through the three longitudinal polar stripes defined by the tyrosine and lysine residues in this sequence.

By making the minimum repeating unit a fourteen amino acid sequence, the crosslinkable residues will alternate in sequence within the three respective polar stripes. By placing apolar amino acids at both ends of the repeating unit, the α-helices and the superhelical structures can be elongated as additional chains will be appropriately configured to add to the ends of these structures.

In addition to these general considerations for the formation of the α-helices of this invention, one can further promote helix formation and stability in the compositions of this invention by including negatively charged group(s) at the N-terminal (+) end, and positively charged group(s) at the C-terminal end of the helix. The effect of these charged groups is to increase the dipole moment across the peptide bonds along the helix, thus promoting helix stability (Shoemaker, et al., (1987) *Nature*, 236:563–567.)

The adhesive matrix of this invention is particularly adapted to allow therapeutic compounds and/or replacement cells to be dispersed within it, so that the matrix may act as a delivery vehicle capable of maintaining compounds at a site of application in vivo. Because the structure of the polypeptide chains of this invention are designed to form α-helices which will cohere in solution, the matrix will have adhesive and cohesive character even in the absence of interchain crosslinking. Thus the strength of the cohesive matrix can be modulated by altering the length of the peptides, and the degree of crosslinking between the chains. This allows the matrix to be useful for a variety of different medical applications.

Of particular interest is the use of the matrix to maintain primary cell lines, especially those capable of secreting the components that make up tendon, ligament and cartilage, at a site of application in vivo. For example, during periodontitis, there is specific loss of extracellular matrix from the ligament that holds the tooth in position. There is also loss of the periodontal ligament fibroblasts that synthesize the extracellular matrix. The ability to deliver replacement cells and/or cell growth promoting factors (e.g., growth factors such as EGF, PDGF, TGF-α, TGF-β, FGF and IGF) to the site of tissue loss, and the ability to have those cells and therapeutic compounds stay at the site of application can have significant impact in the treatment of periodontitis and other diseases that are characterized by tissue loss.

The matrix also may be used to close surgical incisions. The adhesive strength of the matrix may be modulated to correspond to the length of time required for the tissue surfaces to heal. Rapidly healing tissue, such as skin or liver, may require matrices minimally crosslinked, while adhesives used in cornea replacement protocol, which may take up to four months to heal, may require longer repeats and increased crosslinking.

Polypeptide chains of this invention may be synthesized by chemical means, on a solid phase peptide synthesizer, or by recombinant DNA technology, using techniques well known to those of ordinary skill in the art.

EXAMPLE 1

Solid Phase Synthesis

The solid phase peptide synthesis described below follows protocols well known to those of ordinary skill in the art, and is therefore not disclosed in detail herein. The peptides of this invention are synthesized using a general protocol described in U.S. patent application Ser. No. 028,500 (filed Mar. 20, 1987), the disclosure of which is hereby incorporated by reference. Briefly, peptides are synthesized on a Biosearch solid phase peptide synthesizer, using standard operating procedures. Completed chains then are deprotected and purified by HPLC (high pressure liquid chromatography).

A number of different peptides, described in detail below, are synthesized by this method, including positive and negative control peptides for adhesion and cohesion assays:

P150 A 21-amino acid polypeptide having a preferred amino acid sequence of this invention (Sequence Listing ID No. 4):

Ala-Ala-Ala-Lys-Tyr-Lys-Ala-Ala-Ala-Ala-Tyr-
Lys-Tyr-Ala-Ala-Ala-Ala-Lys-Tyr-Lys-Ala

The peptide is designed such that three polar stripes defined by an alternating arrangement of lysine and tyrosine residues are distributed circumferentially about the helix surface. Alanines are chosen for the apolar residues, to favor adoption of an α-helical structure in solution. Chou-Fasman and Garnier-Robson algorithms for predicted secondary structure indicate an α-helical content of between 67% and 100%.

P95 A positive control, modeled after the 10 amino acid repeat unit from mussel glue protein (Sequence Listing ID No. 5):

Ala-Lys-Pro-Ser-Tyr-Xaa$_1$-Xaa$_1$-Thr-Tyr-Lys where Xaa$_1$ is hyroxyproline.

P96 A positive control, also modeled after the mussel glue protein decapeptide. P96 differs from P95 in having three of the repeating decapeptide units of P95:

[P95]$_3$

P68 A negative control, containing lysines, and an amino acid sequence with predicted substantial α-helical character (between 56 and 100%), but having no tyrosine residues (Sequence Listing ID No. 6):

Lys-Glu-Thr-Ala-Ala-Ala-Lys-phe-Glu-Arg-Gln-
His-Asn-Leu-Glu-Asp-Ala-Gly.

EXAMPLE 2

Biological Evaluation.

P150 peptides and appropriate controls are evaluated for their adhesive and cohesive capabilities using the assays described below.

The attachment of mink lung cells to plastic is used to assess the ability of bioadhesive peptides to promote cell adhesion. The peptides are allowed to adsorb onto the surface of a 96-well titer plate from a bicarbonate buffer. The surface is washed with water, and mink lung cells (in serum free media) then applied to the surface. Under the conditions of the assay, mink lung cells do not adhere to the surface of the plate unless the protein or peptide coating the plate exhibits properties of cellular adherence. The adhesion of the cells is followed by visual examination under a microscope.

In this and the following examples, P95, P96 and mussel bioadhesive protein ("Cell Tak"), purchased from Collaborative Research, are used as positive controls. Negative controls are P68 and bovine serum albumin (BSA).

Table 1 shows the relative ability of the proteins and unmodified peptides to promote cellular adherence. As expected, when there is no protein on the plate, or in plates coated with BSA or P68, there is no attachment of any cells. However, in the presence of a known bioadhesive (Mussel Glue Protein), or peptides modeled after the Mussel bioadhesive decapeptide (P95 and P96), there is significant cellular adhesion. Likewise, the novel peptide P150 also exhibits the same magnitude of cell attachment.

TABLE 1

CELL ADHESION WITH SYNTHETIC PEPTIDES

| PROTEIN/PEPTIDE | CELL ADHESION |
|---|---|
| none | − |
| Albumin (BSA) | − |
| Bioadhesive Protein from Mussel ("CellTak") | + |
| P68 | − |
| P95 | + |
| P96 | + |
| P150 | + |

EXAMPLE 3

The Crosslinking (Cohesion) Assay

The peptides are crosslinked chemically, with glutaraldehyde, following the method of Waite, J. H., disclosed in U.S. Pat. No. 4,808,702, filed Jun. 1, 1987, or enzymatically with a tyrosinase enzyme. Crosslinking of proteins and peptides can be monitored visually (for the appearance of a precipitate) as well as by SDS polyacrylamide gel electrophoresis (PAGE), or HPLC.

Figure 3:
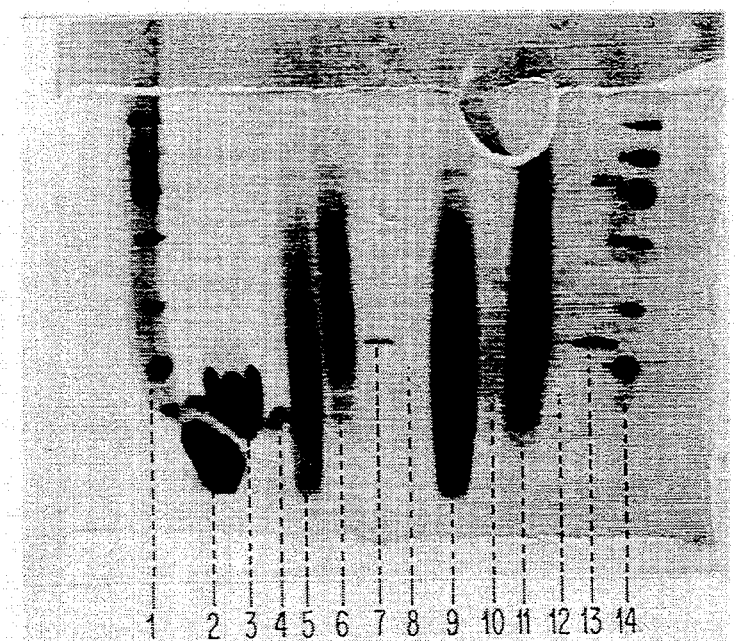
FIG. 3 is a photoreproduction of SDS-PAGE gels illustrating various properties of the cohesive helices of this invention.

Enzymatic crosslinking is performed essentially following the protocol of Marumo et al., 1986, *Biochem, Biophys. Acta*, 872:98. An approximately 10:1 weight ratio of peptide to enzyme is incubated for at least two hours in 50 mM sodium phosphate, pH 7.5. Crude mushroom tyrosinase enzyme, (from Sigma Chemical Co., St. Louis, Mo.) is used in these experiments. To promote crosslinking, other enzymes also may be used, such as catechol 2,3-dioxygenase. FIG. 3 is an illustrative gel (SDS PAGE) of this experiment, performed on various sample peptides. Untreated P150 and P96 peptides (lanes 2 and 3, respectively) migrate to the bottom of the gel. The same peptides form higher order species (visualized as a smear on the gel) after treatment with tyrosinase (P150+ tyrosinase, lanes 5 and 9; P96+ tyrosinase, lanes 6 and 11.) The remaining lanes on the gel are molecular weight standards (lanes 1, 14), the crude tyrosinase enzyme sample alone (lanes 7, 13) or are blank (lanes 4, 8, 12).

Figure 4A:
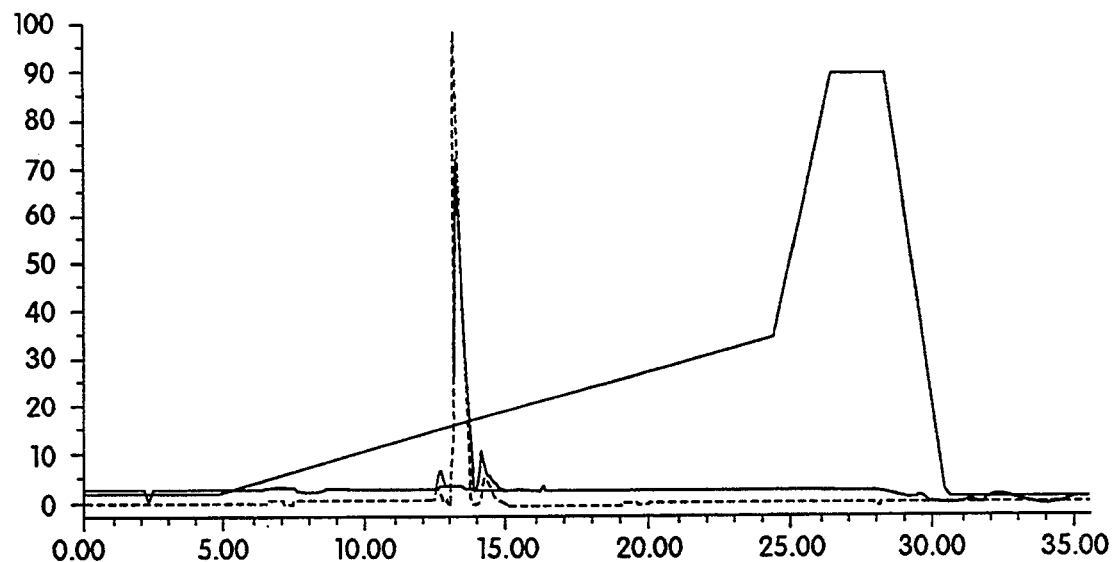
FIGS. 4 (A–B) and 5 (A–B) are HPLC chromatographs of a positive control peptide (P95, FIG. 4) and a negative control peptide (P4, FIG. 5) before (A), and after (B), treatment with mushroom tyrosinase.
Figure 4B:
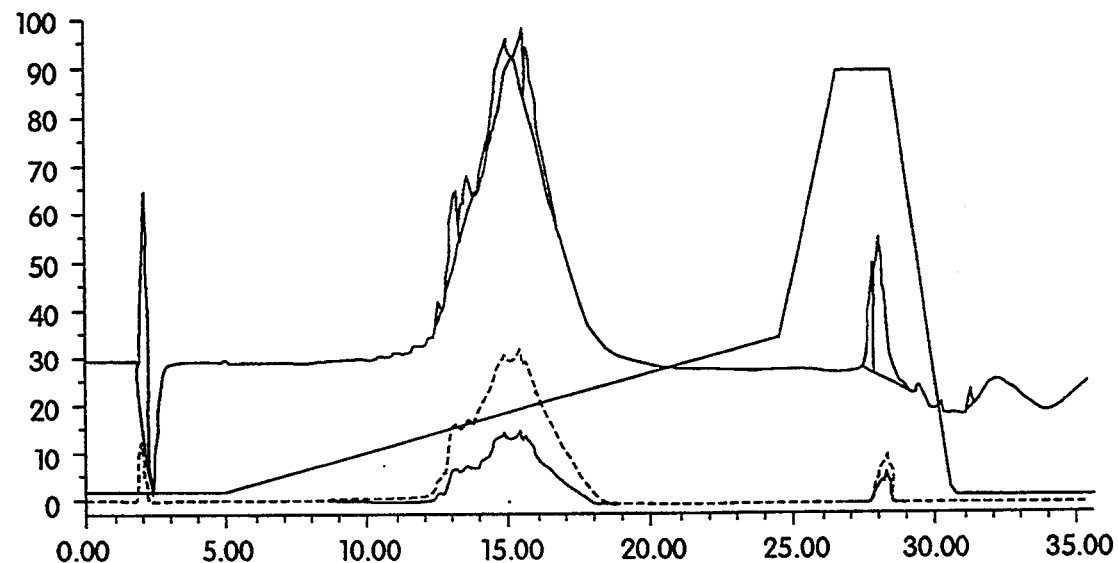
Figure 5A:
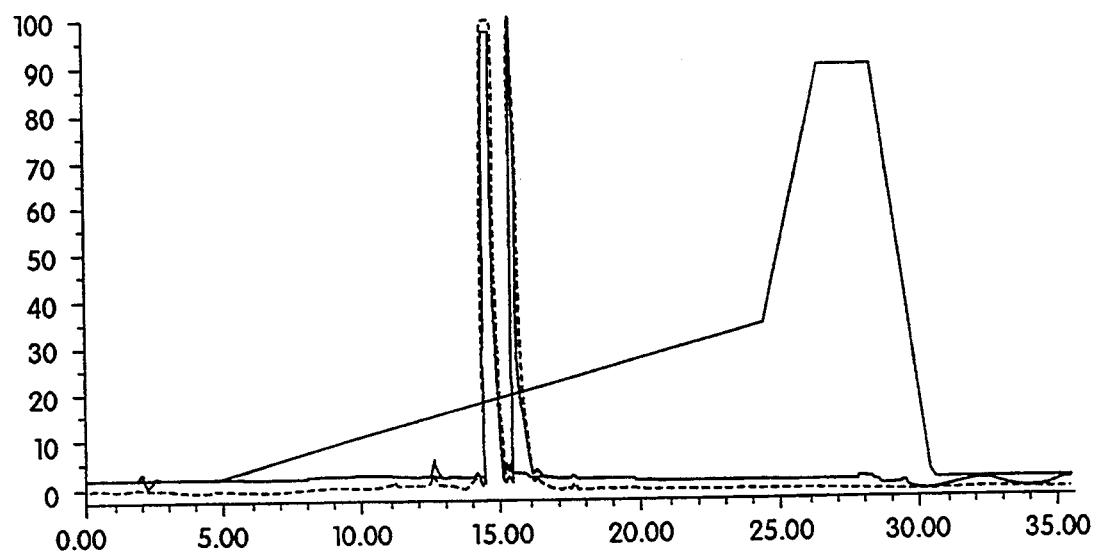
Figure 5B:
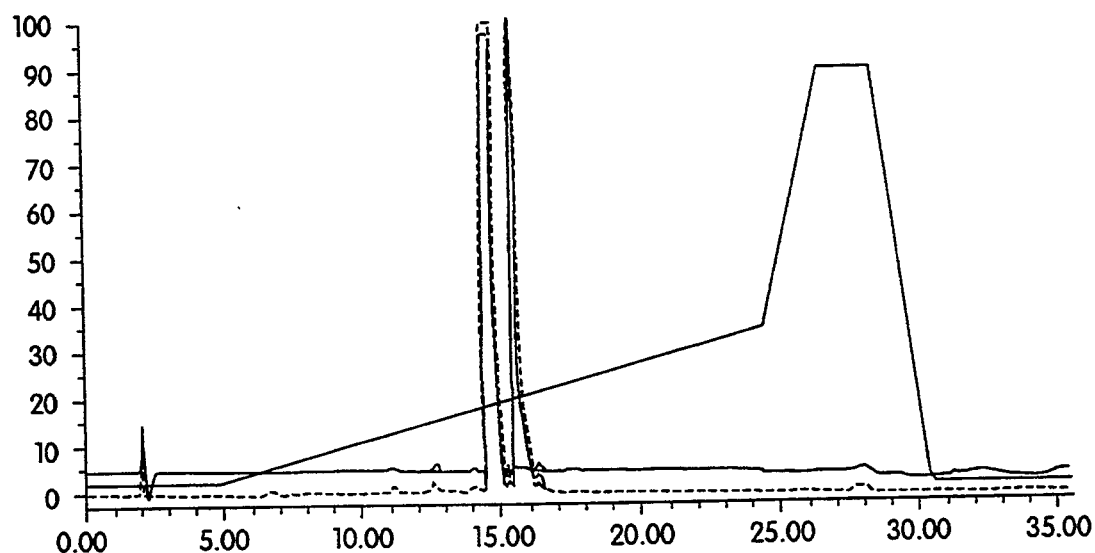

By contrast, negative control peptides that do not include a tyrosine amino acid are not affected by treatment with tyrosinase enzyme, as illustrated in FIGS. 4 and 5. FIGS. 4 and 5 are HPLC chromatographs of two different sample peptides before (panel A), and after (panel B), treatment with tyrosinase enzyme. Proteins are eluted using an acetonitrile gradient. FIG. 4 shows the effect of tyrosinase enzyme treatment on a positive control (P95). Crosslinking with tyrosinase enzyme results in a substantial change in peak absorbance at 15 minutes, as shown in FIG. 4B. FIG. 5 shows the effect of tryosinase enzyme treatment on a negative control peptide (P4, a small negative control peptide that does not contain any tyrosine residues). Here treatment with tyrosinase enzyme has no effect on the peak absorbance at 15 minutes, as shown in FIG. 5B.

In order to determine if the cellular attachment properties exhibited by the peptides are maintained during crosslinking, various test peptides (and BSA and the mussel glue protein) are chemically crosslinked using 50% glutaraldehyde prior to their adsorption onto the titer plate surface. All peptides form higher order aggregates and precipitates after treatment with gluteraldehyde, as indicated by precipitate formation and visualization of high molecular weight aggregates on SDS polyacrylamide gels.

As can be seen in Table 2, chemical crosslinking does not promote cell attachment in the negative controls (BSA and P68) and it does not interfere with cellular adhesion properties of the mussel glue protein or peptides P95 and P150. Moreover, the adhesive properties of P150 alone are significantly enhanced by crosslinking.

TABLE 2

CELL ADHESION IN THE PRESENCE OF CROSSLINKING

| PROTEIN/PEPTIDE | CELL ADHESION |
|---|---|
| none | − |
| Albumin (BSA) and glutaraldehyde | − |
| Bioadhesive Protein from Mussel and glutaraldehyde | + |
| P95 and tyrosinase and glutaraldehyde | +/− |
| P150 and tyrosinase and glutaraldehyde | ++ |

Example 4.

Preparation of Recombinant P150 Genes

The compositions of this invention also may be synthesized by recombinant DNA technology using general techniques well known to those of ordinary skill in the art. The processes for manipulating, amplifying, and recombining DNA which encode amino acid sequences of interest are generally well known in the art and are not described in detail herein. Methods of identifying and isolating genes encoding proteins of interest, or for constructing such genes, are well understood and developed. These processes are described in the patent and other literature (see for example, U.S. Pat. No. 4,431,739). In general, the methods involve selecting genetic material coding for amino acids which define polypeptides of interest according to the genetic code.

Accordingly, in addition to the DNA construction principles disclosed herein, the polypeptides of this invention can be synthesized recombinantly using any of a number of different, known construction techniques and restriction enzymes. Various promoter sequences and other regulatory DNA sequences used in achieving expression, and various types of host cells are available, including animal cell lines and prokaryotic cells. A currently preferred host cell is *E. coli*. Various types of vectors may be used, such as plasmids and viruses, including animal viruses and bacteriophages, and combinations thereof. The vectors also may exploit various marker genes well known to the art which impart to a successfully transfected cell a detectable phenotypic property that can be used to identify which of a family of cells has successfully incorporated the recombinant DNA of the vector. Given the foregoing state of the genetic engineering art, skilled persons are enabled to practice the invention disclosed herein in view of this disclosure.

The core repeat unit of peptide P150 used in the gene designs described below is a 14-mer of the following sequence (Sequence Listing ID No. 3):

Ala-Ala-Ala-Lys-Tyr-Lys-Ala-Ala-Ala-Tyr-Lys-Tyr-Ala.

A pair of synthetic oligonucleotides of about 60 residues (see FIG. 6A and/or 6B, Sequence Listing ID Nos. 7 and/or 9, respectively) and which encode this basic building block are synthesized using a conventional, automated, polynucleotide synthesizer (e.g., a Milligen 7500 DNA Synthesizer). The synthetic oligonucleotides then are deprotected, purified by conventional methods, and cloned into an appropriate vector (e.g., a pUC-type cloning vector), using the general cloning technology understood in the art, (see, for example, Yanisch-Perron, C. et al., (1985) *Gene* 33:103–119).

The gene design given below and illustrated in FIG. 6 (A and B) incorporates the following considerations: the gene starts with a methionine, ends in a stop codon, and is flanked by restriction sites for splicing into appropriate expression vectors. It also contains an arrangement of restriction sites that allow tandemizing and further extensions of the repeats. Two versions can be made which are used to produce a first tandem with unique internal restriction sites. The sequence also contains an AlwNI site which allows polymerization of fragments in a unidirectional way due to the nature of the cohesive end of this restriction site.

Using the two nucleotide sequence versions shown in FIG. 6, a tandem sequence is readily generated by splicing the 3' PvuII end of the Version 1 gene (FIG. 6A, Sequence Listing ID Nos. 7 and 8) with the 5' PvuII end of the Version 2 gene (FIG. 6B, Sequence Listing ID Nos. 9 and 10). After combining both strands one obtains the tandem gene shown in FIG. 7 (Sequence ID Nos. 11 and 12).

One then can insert one or more fragments containing the tandem gene of FIG. 5 into one of the Pst sites generated by a partial PstI digest to obtain a gene encoding, for example, four repeats of the 14 amino acid P150 core sequence (see FIG. 8).

The general procedure described herein allows the synthesis of genes that encode any number of P150 core region repeats. The accuracy of the gene assembly is evaluated by conventional Sanger sequencing methods. If changes in the amino acid sequence are desired (for example, to enhance protein solubility), this can be done by site-directed mutagenesis on the basic P150 unit molecule prior to extensive tandemizing.

The direct expression of the P150 proteins in *E. coli* is possible using methionine as the first amino acid. Protein expression also can be enhanced using the polypeptide expression technology described in U.S. patent application Ser. No. 028,500 (filed Mar. 20, 1987, incorporated by reference, supra), and U.S. Pat. No. 4,743,679, the disclosure of which is hereby incorporated by reference.

Using this technology to over-express the peptides of this invention results in the precipitation of the desired protein as a fusion protein within the bacteria to form inclusion bodies. The inclusion bodies can be recovered easily from the lysed bacteria and the fusion protein renatured using a mixture of reducing and denaturing agents. The protein leader sequence can be removed subsequently from the expressed protein by chemical or enzymatic cleavage methods and the resulting protein purified by sequential chromatography.

Additional Examples

The "gluing" ability of the compositions of this invention is readily measured using the procedure of Harris et al. (1988, *Laryngoscope* 98:731) wherein the composition is applied to two surfaces of fresh tissue (dura), the surfaces are contacted to allow bond formation between the surfaces, and the amount of weight required to break the bond is determined.

The drug delivery properties of the compositions of this invention can also be readily evaluated in an in vitro mitogenesis assay. The minimum concentration of crosslinking agent (preferably tyrosinase) required for matrix formation is first determined. Using this concentration, tyrosinase enzyme and an appropriate growth factor are mixed with the adhesive protein to be evaluated in 96-well cell culture dishes. After matrix formation, the plates are rinsed and incubated with confluent 3T3 fibroblast cells and labelled thymidine. The presence of growth factors induces mitogenesis, allowing the cells to incorporate labelled thymidine. The amount of thymidine incorporated is quantitated by autoradiography or liquid scintillation counting to determine the degree of cell stimulation.

Cell replication within the matrix can be measured by following the rate of incorporation of a labelled nucleotide into DNA using standard methodology and, for example, triturated thymidine. Samples comprising the composition of this invention, a known concentration of replacement cells and a tyrosinase enzyme first are incubated in a growth media, in the presence of $^3$H-thymidine. The samples then are lyophilized, and dry weights determined on an analytical balance. Samples are subsequently solubilized in 70% formic acid overnight at 70 C, neutralized, and counted in a liquid scintillation counter. Growing cells will incorporate the labelled thymidine and the amount of incorporated labelled thymidine associated with the matrix will be proportional to the degree of cell replication occurring.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:

(A) LENGTH: 10 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: N-terminal (ix) FEATURE:
            (A) NAME/KEY: Peptide
            (B) LOCATION: 1..10
            (D) OTHER INFORMATION: /note="Pro #osoft Corp
                3- hydroxyproline or 4-hydroxyproline and Xaa is
                3,4- dihydroxylphenylalanine"

(x) PUBLICATION INFORMATION:
            (A) AUTHORS: Waite,, J. H.
                Housley, Timothy J.
                Tanzer, Marvin L.
            (B) TITLE: Peptide Repeats in a Mussel Glue
                Protein:Theme and Variations
            (C) JOURNAL: Biochemistry
            (D) VOLUME: 24
            (E) ISSUE: 19
            (F) PAGES: 5010-5014
            (G) DATE: 1985
            (K) RELEVANT RESIDUES IN SEQ ID NO:1: FROM 1 TO 10

(xi) SEQUENCE DESCRIPTION: SEQ ID NO:1:

Ala  Lys  Pro  Ser  Tyr  Pro  Pro  Thr  Xaa  Lys
    1                  5                        10

(2) INFORMATION FOR SEQ ID NO:2:

(i) SEQUENCE CHARACTERISTICS:
            (A) LENGTH: 14 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: N-terminal (ix) FEATURE:
            (A) NAME/KEY: Protein
            (B) LOCATION: 1..14

(xi) SEQUENCE DESCRIPTION: SEQ ID NO:2:

Xaa  Xaa  Xaa  Xaa  Xaa  Xaa  Xaa  Xaa  Xaa  Xaa  Xaa  Xaa  Xaa  Xaa
    1                  5                        10

(2) INFORMATION FOR SEQ ID NO:3:

(i) SEQUENCE CHARACTERISTICS:
            (A) LENGTH: 14 amino acids
            (B) TYPE: amino acid
            (C) STRANDEDNESS: single
            (D) TOPOLOGY: linear (ii) MOLECULE TYPE: protein (iii) HYPOTHETICAL: NO (iv) ANTI-SENSE: NO (v) FRAGMENT TYPE: N-terminal (ix) FEATURE:

(A) NAME/KEY: Protein
(B) LOCATION: 1..14
(D) OTHER INFORMATION: /note="The sequence may be repeated up to at least about 100 times in a polypeptide chain"

(xi) SEQUENCE DESCRIPTION: SEQ ID NO:3:

```
Ala Ala Ala Lys Tyr Lys Ala Ala Ala Ala Tyr Lys Tyr Ala
1               5                   10
```

(2) INFORMATION FOR SEQ ID NO:4:

(i) SEQUENCE CHARACTERISTICS:
    (A) LENGTH: 21 amino acids
    (B) TYPE: amino acid
    (C) STRANDEDNESS: single
    (D) TOPOLOGY: linear (ii) MOLECULE TYPE: protein (iii) HYPOTHETICAL: NO (iv) ANTI-SENSE: NO (v) FRAGMENT TYPE: N-terminal (xi) SEQUENCE DESCRIPTION: SEQ ID NO:4:

```
Ala Ala Ala Lys Tyr Lys Ala Ala Ala Ala Tyr Lys Tyr Ala Ala Ala
1               5                   10                  15

Ala Lys Tyr Lys Ala
            20
```

(2) INFORMATION FOR SEQ ID NO:5:

(i) SEQUENCE CHARACTERISTICS:
    (A) LENGTH: 10 amino acids
    (B) TYPE: amino acid
    (C) STRANDEDNESS: single
    (D) TOPOLOGY: linear (ii) MOLECULE TYPE: peptide (iii) HYPOTHETICAL: NO (iv) ANTI-SENSE: NO (v) FRAGMENT TYPE: N-terminal (ix) FEATURE:
    (A) NAME/KEY: Peptide
    (B) LOCATION: 1..10
    (D) OTHER INFORMATION: /note="Prolines at amino acid residues 6 and 7 are either 3-hydroxyproline or 4- hydroxyproline"

(xi) SEQUENCE DESCRIPTION: SEQ ID NO:5:

```
Ala Lys Pro Ser Tyr Pro Pro Thr Tyr Lys
1               5                   10
```

(2) INFORMATION FOR SEQ ID NO:6:

(i) SEQUENCE CHARACTERISTICS:
    (A) LENGTH: 18 amino acids
    (B) TYPE: amino acid
    (C) STRANDEDNESS: single
    (D) TOPOLOGY: linear (ii) MOLECULE TYPE: peptide (iii) HYPOTHETICAL: NO (iv) ANTI-SENSE: NO (v) FRAGMENT TYPE: N-terminal (x i) SEQUENCE DESCRIPTION: SEQ ID NO:6:

Lys Glu Thr Ala Ala Ala Lys Phe Glu Arg Gln His Asn Leu Glu Asp
1               5                   10                  15

Ala Gly (2) INFORMATION FOR SEQ ID NO:7:

(i) SEQUENCE CHARACTERISTICS:
      (A) LENGTH: 63 base pairs
      (B) TYPE: nucleic acid
      (C) STRANDEDNESS: double
      (D) TOPOLOGY: unknown (i i) MOLECULE TYPE: cDNA (i i i) HYPOTHETICAL: NO (i v) ANTI-SENSE: NO (v) FRAGMENT TYPE: N-terminal (i x) FEATURE:
      (A) NAME/KEY: CDS
      (B) LOCATION: 3..59

(x i) SEQUENCE DESCRIPTION: SEQ ID NO:7:

CC ATG GCT GCT GCA GCT AAG TAC AAA GCA GCC GCT GCA TAT AAA TAT   47
   Met Ala Ala Ala Ala Lys Tyr Lys Ala Ala Ala Ala Tyr Lys Tyr
   1               5                   10                  15

GCC GCA GCT GGC TAGC   63
Ala Ala Ala Gly (2) INFORMATION FOR SEQ ID NO:8:

(i) SEQUENCE CHARACTERISTICS:
      (A) LENGTH: 19 amino acids
      (B) TYPE: amino acid
      (D) TOPOLOGY: linear (i i) MOLECULE TYPE: protein (x i) SEQUENCE DESCRIPTION: SEQ ID NO:8:

Met Ala Ala Ala Ala Lys Tyr Lys Ala Ala Ala Ala Tyr Lys Tyr Ala
1               5                   10                  15

Ala Ala Gly (2) INFORMATION FOR SEQ ID NO:9:

(i) SEQUENCE CHARACTERISTICS:
      (A) LENGTH: 63 base pairs
      (B) TYPE: nucleic acid
      (C) STRANDEDNESS: double
      (D) TOPOLOGY: unknown (i i) MOLECULE TYPE: cDNA (i i i) HYPOTHETICAL: NO (i v) ANTI-SENSE: NO (v) FRAGMENT TYPE: N-terminal (i x) FEATURE:
      (A) NAME/KEY: CDS
      (B) LOCATION: 3..59

(x i) SEQUENCE DESCRIPTION: SEQ ID NO:9:

CC ATG GCA GCA GCT GCT AAG TAC AAA GCA GCC GCT GCA TAT AAA TAT   47
   Met Ala Ala Ala Ala Lys Tyr Lys Ala Ala Ala Ala Tyr Lys Tyr
   1               5                   10                  15

```
GCT GCT GCA GGC TAGC                                                              63
Ala Ala Ala Gly
```

( 2 ) INFORMATION FOR SEQ ID NO:10:

( i ) SEQUENCE CHARACTERISTICS:
    ( A ) LENGTH: 19 amino acids
    ( B ) TYPE: amino acid
    ( D ) TOPOLOGY: linear ( i i ) MOLECULE TYPE: protein ( x i ) SEQUENCE DESCRIPTION: SEQ ID NO:10:

```
Met Ala Ala Ala Ala Lys Tyr Lys Ala Ala Ala Ala Tyr Lys Tyr Ala
 1               5                   10                  15

Ala Ala Gly
```

( 2 ) INFORMATION FOR SEQ ID NO:11:

( i ) SEQUENCE CHARACTERISTICS:
    ( A ) LENGTH: 105 base pairs
    ( B ) TYPE: nucleic acid
    ( C ) STRANDEDNESS: double
    ( D ) TOPOLOGY: both ( i i ) MOLECULE TYPE: cDNA ( i i i ) HYPOTHETICAL: NO ( i v ) ANTI-SENSE: NO ( v ) FRAGMENT TYPE: N-terminal ( i x ) FEATURE:
    ( A ) NAME/KEY: CDS
    ( B ) LOCATION: 3..101

( x i ) SEQUENCE DESCRIPTION: SEQ ID NO:11:

```
CC ATG GCT GCT GCA GCT AAG TAC AAA GCA GCC GCT GCA TAT AAA TAT              47
   Met Ala Ala Ala Ala Lys Tyr Lys Ala Ala Ala Ala Tyr Lys Tyr
    1               5                   10                  15

GCC GCA GCT GCT AAG TAC AAA GCA GCC GCT GCA TAT AAA TAT GCT GCT             95
Ala Ala Ala Ala Lys Tyr Lys Ala Ala Ala Ala Tyr Lys Tyr Ala Ala
            20                  25                  30

GCA GGC TAGC                                                               105
Ala Gly
```

( 2 ) INFORMATION FOR SEQ ID NO:12:

( i ) SEQUENCE CHARACTERISTICS:
    ( A ) LENGTH: 33 amino acids
    ( B ) TYPE: amino acid
    ( D ) TOPOLOGY: linear ( i i ) MOLECULE TYPE: protein ( x i ) SEQUENCE DESCRIPTION: SEQ ID NO:12:

```
Met Ala Ala Ala Ala Lys Tyr Lys Ala Ala Ala Ala Tyr Lys Tyr Ala
 1               5                   10                  15

Ala Ala Ala Lys Tyr Lys Ala Ala Ala Ala Tyr Lys Tyr Ala Ala Ala
            20                  25                  30

Gly
```

What is claimed is:

1. A synthetic composition for use as an adhesive in aqueous environment comprising:
   a plurality of polypeptide chains, each polypeptide chain having a helical structure in aqueous environments and one or more copies of the amino acid sequence (Seq. Listing ID No. 2):

$(Xaa_1\text{-}Xaa_1\text{-}Xaa_1\text{-}Xaa_2\text{-}Xaa_3\text{-}Xaa_2\text{-}Xaa_1\text{-}Xaa_1\text{-}Xaa_1\text{-}$
$Xaa_1\text{-}Xaa_3\text{-}Xaa_2\text{-}Xaa_3\text{-}Xaa_1)_b$ wherein b is a number from 1 to 100; each $Xaa_1$ is independently selected from the group of apolar amino acids consisting of leucine, isoleucine, valine, alanine, glycine, phenylalanine, and methionine; each $Xaa_2$ and $Xaa_3$ is an independently selected crosslinkable, surface adherable amino acid adapted to form interchain crosslinks between said helical polypeptide chains such that, when crosslinked, said plurality of polypeptide chains form an insoluble matrix having adhesive properties sufficient to adhere cells in an aqueous environment.

2. The composition of claim 1 wherein the polypeptide chains comprise one or more copies of the amino acid sequence (Seq. Listing ID No. 3):

$(Ala\text{-}Ala\text{-}Ala\text{-}Lys\text{-}Tyr\text{-}Lys\text{-}Ala\text{-}Ala\text{-}Ala\text{-}Ala\text{-}Tyr\text{-}$
$Lys\text{-}Tyr\text{-}Ala)_b$ where b is a number from 1 to 100.

3. A synthetic matrix having substantial adhesive properties in aqueous environments, said matrix comprising:
a plurality of crosslinked polypeptide chains, each polypeptide chain having a helical structure in aqueous environments and one or more copies of the amino acid sequence (Seq. Listing ID No. 2)

$(Xaa_1\text{-}Xaa_1\text{-}Xaa_1\text{-}Xaa_2\text{-}Xaa_3\text{-}Xaa_2\text{-}Xaa_1\text{-}Xaa_1\text{-}$
$Xaa_1 Xaa_1\text{-}Xaa_3\text{-}Xaa_2\text{-}Xaa_3\text{-}Xaa_1)_b$ wherein b is a number from 1 to 100; each $Xaa_1$ is independently selected from the group of apolar amino acids consisting of leucine, isoleucine, valine, alanine, glycine, phenylalanine, and methionine, and each $Xaa_2$ and $Xaa_3$ is an independently selected crosslinkable, polar, surface adherable amino acid adapted to form interchain crosslinks between said helical polypeptide chains, the crosslinked structures forming an insoluble matrix having adhesive properties sufficient to adhere cells in an aqueous environment.

4. The polypeptide chains of claim 1 or 3 wherein the apolar amino acids comprise alanine residues.

5. The polypeptide chains of claim 1 or 3 wherein the crosslinkable amino acids comprise tyrosine and lysine residues.

6. The composition of claim 1 wherein the polypeptide chains are covalently crosslinked.

7. The polypeptide chains of claim 3 or 6 crosslinked by glutaraldehyde.

8. The polypeptide of claim 3 or 6 crosslinked by treatment with a tyrosinase enzyme.

9. A synthetic matrix capable of maintaining a therapeutic compound at a site of application in vivo, said matrix comprising the crosslinked synthetic polypeptide chains of claims 3 and a therapeutic compound dispersed therein.

10. The synthetic matrix of claim 3 or 9 wherein said polypeptide chains comprise one or more copies of the amino acid sequence of (Seq. ID No. 3):

$(Ala\text{-}Ala\text{-}Ala\text{-}Lys\text{-}Tyr\text{-}Lys\text{-}Ala\text{-}Ala\text{-}Ala\text{-}Ala\text{-}Tyr\text{-}$
$Lys\text{-}Tyr\text{-}Ala)_b$ where b is a number from 1 to 100.

11. An artificial adhesive matrix for filling tissue gaps, the matrix comprising the crosslinked synthetic polypeptide chains of claims 3 or 9.

12. A composition for stimulating cell growth comprising the crosslinked synthetic polypeptide chains of claim 3 or 9 and a compound capable of stimulating cell growth dispersed among said crosslinked polypeptide chains.

13. The composition of claim 12 wherein said compound is a growth factor selected from the group consisting of: EGF, IGF, TGF-α, TGF-β, PDGF, and FGF.

---

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( i x ) FEATURE:
        ( A ) NAME/KEY: Peptide
        ( B ) LOCATION: 1..10
        ( D ) OTHER INFORMATION: /note="Pro #osoft Corp
            3- hydroxyproline or 4-hydroxyproline and Xaa is
            3,4- dihydroxylphenylalanine"

( x ) PUBLICATION INFORMATION:
        ( A ) AUTHORS: Waite,, J. H.
                     Housley, Timothy J.

Tanzer, Marvin L.
- (B) TITLE: Peptide Repeats in a Mussel Glue Protein:Theme and Variations
- (C) JOURNAL: Biochemistry
- (D) VOLUME: 24
- (E) ISSUE: 19
- (F) PAGES: 5010-5014
- (G) DATE: 1985
- (K) RELEVANT RESIDUES IN SEQ ID NO:1: FROM 1 TO 10

(xi) SEQUENCE DESCRIPTION: SEQ ID NO:1:

```
Ala Lys Pro Ser Tyr Pro Pro Thr Xaa Lys
1               5                   10
```

(2) INFORMATION FOR SEQ ID NO:2:

- (i) SEQUENCE CHARACTERISTICS:
    - (A) LENGTH: 14 amino acids
    - (B) TYPE: amino acid
    - (C) STRANDEDNESS: single
    - (D) TOPOLOGY: linear

- (ii) MOLECULE TYPE: peptide

- (iii) HYPOTHETICAL: NO

- (iv) ANTI-SENSE: NO

- (v) FRAGMENT TYPE: N-terminal

- (ix) FEATURE:
    - (A) NAME/KEY: Protein
    - (B) LOCATION: 1..14

(xi) SEQUENCE DESCRIPTION: SEQ ID NO:2:

```
Xaa Xaa Xaa Xaa Xaa Xaa Xaa Xaa Xaa Xaa Xaa Xaa Xaa Xaa
1               5                   10
```

(2) INFORMATION FOR SEQ ID NO:3:

- (i) SEQUENCE CHARACTERISTICS:
    - (A) LENGTH: 14 amino acids
    - (B) TYPE: amino acid
    - (C) STRANDEDNESS: single
    - (D) TOPOLOGY: linear

- (ii) MOLECULE TYPE: protein

- (iii) HYPOTHETICAL: NO

- (iv) ANTI-SENSE: NO

- (v) FRAGMENT TYPE: N-terminal

- (ix) FEATURE:
    - (A) NAME/KEY: Protein
    - (B) LOCATION: 1..14
    - (D) OTHER INFORMATION: /note="The sequence may be repeated up to at least about 100 times in a polypeptide chain"

(xi) SEQUENCE DESCRIPTION: SEQ ID NO:3:

```
Ala Ala Ala Lys Tyr Lys Ala Ala Ala Ala Tyr Lys Tyr Ala
1               5                   10
```

(2) INFORMATION FOR SEQ ID NO:4:

- (i) SEQUENCE CHARACTERISTICS:
    - (A) LENGTH: 21 amino acids
    - (B) TYPE: amino acid
    - (C) STRANDEDNESS: single
    - (D) TOPOLOGY: linear

- (ii) MOLECULE TYPE: protein

- (iii) HYPOTHETICAL: NO ( i v ) ANTI-SENSE: NO ( v ) FRAGMENT TYPE: N-terminal ( x i ) SEQUENCE DESCRIPTION: SEQ ID NO:4:

```
Ala Ala Ala Lys Tyr Lys Ala Ala Ala Ala Tyr Lys Tyr Ala Ala Ala
1               5                   10                  15
Ala Lys Tyr Lys Ala
            20
```

( 2 ) INFORMATION FOR SEQ ID NO:5:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( i x ) FEATURE:
        ( A ) NAME/KEY: Peptide
        ( B ) LOCATION: 1..10
        ( D ) OTHER INFORMATION: /note="Prolines at amino acid
        residues 6 and 7 are either 3-hydroxyproline or
        4- hydroxyproline"

( x i ) SEQUENCE DESCRIPTION: SEQ ID NO:5:

```
Ala Lys Pro Ser Tyr Pro Pro Thr Tyr Lys
1               5                   10
```

( 2 ) INFORMATION FOR SEQ ID NO:6:

( i ) SEQUENCE CHARACTERISTICS:
        ( A ) LENGTH: 18 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:6:

```
Lys Glu Thr Ala Ala Ala Lys Phe Glu Arg Gln His Asn Leu Glu Asp
1               5                   10                  15
Ala Gly
```

( 2 ) INFORMATION FOR SEQ ID NO:7:

( i ) SEQUENCE CHARACTERISTICS:
        ( A ) LENGTH: 63 base pairs
        ( B ) TYPE: nucleic acid
        ( C ) STRANDEDNESS: double
        ( D ) TOPOLOGY: unknown ( i i ) MOLECULE TYPE: cDNA ( i i i ) HYPOTHETICAL: NO ( i v ) ANTI-SENSE: NO ( v ) FRAGMENT TYPE: N-terminal ( i x ) FEATURE:
        ( A ) NAME/KEY: CDS
        ( B ) LOCATION: 3..59

( x i ) SEQUENCE DESCRIPTION: SEQ ID NO:7:

```
CC ATG GCT GCT GCA GCT AAG TAC AAA GCA GCC GCT GCA TAT AAA TAT      47
   Met Ala Ala Ala Ala Lys Tyr Lys Ala Ala Ala Ala Tyr Lys Tyr
   1               5                   10                  15

GCC GCA GCT GGC TAGC                                                63
Ala Ala Ala Gly
```

( 2 ) INFORMATION FOR SEQ ID NO:8:

( i ) SEQUENCE CHARACTERISTICS:
        ( A ) LENGTH: 19 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

```
Met Ala Ala Ala Ala Lys Tyr Lys Ala Ala Ala Ala Tyr Lys Tyr Ala
1               5                   10                  15

Ala Ala Gly
```

( 2 ) INFORMATION FOR SEQ ID NO:9:

( i ) SEQUENCE CHARACTERISTICS:
        ( A ) LENGTH: 63 base pairs
        ( B ) TYPE: nucleic acid
        ( C ) STRANDEDNESS: double
        ( D ) TOPOLOGY: unknown ( i i ) MOLECULE TYPE: cDNA ( i i i ) HYPOTHETICAL: NO ( i v ) ANTI-SENSE: NO ( v ) FRAGMENT TYPE: N-terminal ( i x ) FEATURE:
        ( A ) NAME/KEY: CDS
        ( B ) LOCATION: 3..59

( x i ) SEQUENCE DESCRIPTION: SEQ ID NO:9:

```
CC ATG GCA GCA GCT GCT AAG TAC AAA GCA GCC GCT GCA TAT AAA TAT      47
   Met Ala Ala Ala Ala Lys Tyr Lys Ala Ala Ala Ala Tyr Lys Tyr
   1               5                   10                  15

GCT GCT GCA GGC TAGC                                                63
Ala Ala Ala Gly
```

( 2 ) INFORMATION FOR SEQ ID NO:10:

( i ) SEQUENCE CHARACTERISTICS:
        ( A ) LENGTH: 19 amino acids
        ( B ) TYPE: amino acid
        ( D ) TOPOLOGY: linear ( i i ) MOLECULE TYPE: protein ( x i ) SEQUENCE DESCRIPTION: SEQ ID NO:10:

```
Met Ala Ala Ala Ala Lys Tyr Lys Ala Ala Ala Ala Tyr Lys Tyr Ala
1               5                   10                  15

Ala Ala Gly
```

( 2 ) INFORMATION FOR SEQ ID NO:11:

( i ) SEQUENCE CHARACTERISTICS:
  ( A ) LENGTH: 105 base pairs
  ( B ) TYPE: nucleic acid
  ( C ) STRANDEDNESS: double
  ( D ) TOPOLOGY: both ( i i ) MOLECULE TYPE: cDNA ( i i i ) HYPOTHETICAL: NO ( i v ) ANTI-SENSE: NO ( v ) FRAGMENT TYPE: N-terminal ( i x ) FEATURE:
  ( A ) NAME/KEY: CDS
  ( B ) LOCATION: 3..101

( x i ) SEQUENCE DESCRIPTION: SEQ ID NO:11:

```
CC ATG GCT GCT GCA GCT AAG TAC AAA GCA GCC GCT GCA TAT AAA TAT          47
   Met Ala Ala Ala Ala Lys Tyr Lys Ala Ala Ala Ala Tyr Lys Tyr
   1               5                   10                  15

GCC GCA GCT GCT AAG TAC AAA GCA GCC GCT GCA TAT AAA TAT GCT GCT         95
Ala Ala Ala Ala Lys Tyr Lys Ala Ala Ala Ala Tyr Lys Tyr Ala Ala
                20                  25                  30

GCA GGC TAGC                                                           105
Ala Gly
```

( 2 ) INFORMATION FOR SEQ ID NO:12:

( i ) SEQUENCE CHARACTERISTICS:
  ( A ) LENGTH: 33 amino acids
  ( B ) TYPE: amino acid
  ( D ) TOPOLOGY: linear ( i i ) MOLECULE TYPE: protein ( x i ) SEQUENCE DESCRIPTION: SEQ ID NO:12:

```
Met Ala Ala Ala Ala Lys Tyr Lys Ala Ala Ala Ala Tyr Lys Tyr Ala
1               5                   10                  15

Ala Ala Ala Lys Tyr Lys Ala Ala Ala Ala Tyr Lys Tyr Ala Ala Ala
                20                  25                  30

Gly
```

* * * * *